United States Patent [19]
Makino et al.

[11] Patent Number: 5,555,767
[45] Date of Patent: Sep. 17, 1996

[54] LIQUID MIXING METHOD

[75] Inventors: Yoshihiko Makino; Yoshio Saito; Osamu Seshimoto, all of Saitama-ken, Japan

[73] Assignee: Fuji Photo Film Co., Ltd., Kanagawa-ken, Japan

[21] Appl. No.: 390,035

[22] Filed: Feb. 17, 1995

[30] Foreign Application Priority Data

Feb. 25, 1994 [JP] Japan ................................ 6-028324

[51] Int. Cl.⁶ ............................................. G01N 1/38
[52] U.S. Cl. ..................... 73/863; 73/864.01; 436/179; 436/175
[58] Field of Search ............................ 73/863, 864.01; 436/174, 175, 179

[56] References Cited

U.S. PATENT DOCUMENTS

| | | |
|---|---|---|
| 3,855,867 | 12/1974 | Roach . |
| 4,347,875 | 9/1982 | Columbus ............................ 141/18 |
| 4,554,839 | 11/1985 | Hewett et al. .................. 73/864.16 |
| 4,774,055 | 9/1988 | Wakatake et al. ................ 422/64 |
| 4,827,780 | 5/1989 | Sarrine et al. ................. 73/864.21 |
| 5,314,661 | 5/1994 | Mulqueen ........................ 422/57 |
| 5,314,663 | 5/1994 | Mimura ...................... 436/174 X |
| 5,389,339 | 2/1995 | Petschek et al. ................. 422/64 |
| 5,452,619 | 9/1995 | Kawanase et al. ............. 73/864.01 |

FOREIGN PATENT DOCUMENTS

| | | |
|---|---|---|
| 128850 | 8/1982 | Japan . |
| 95358 | 5/1985 | Japan . |
| 188850 | 9/1985 | Japan . |
| 66466 | 3/1988 | Japan . |
| 6467 | 1/1992 | Japan . |
| WO93/07495 | 4/1993 | WIPO . |

OTHER PUBLICATIONS

*Patent Abstracts of Japan* Grp. P216, vol. 7, No. 184 Abs pub. date Aug. 13, 1983 (58–85168) "Autometical Chemical Analyzer".
*Patent Abstracts of Japan* Grp. P661, vol. 12, No. 32 Abs pub. date Jan. 30, 1988 (62–184357) "Stirring Method for Liquid by Pipette".
*Patent Abstracts of Japan*, Grp. C0832, vol. 15, No. 193, Abs. pub date May 17, 1991 (3–49676) "Automated Apparatus for Determination of MIC and Count of Viable Bacteria and Method for Automatic Determination".
*Patent Abstracts of Japan* Grp. P1772, vol. 18, No. 384 Abs pub date Jul. 19, 1994 (6–109740) "Immunity Nephelometry Analyzing Method".

*Primary Examiner*—Thomas P. Noland
*Attorney, Agent, or Firm*—McAulay Fisher Nissen Goldberg & Kiel, LLP

[57] ABSTRACT

In a method for mixing a small amount of a liquid sample with a second liquid, the liquid sample is first fed into a mixing vessel. Thereafter, the second liquid is discharged from an orifice of a second liquid pipette tip into the vessel, and the liquid sample and the second liquid are thereby stirred with each other. The small amount of the liquid sample is thus efficiently stirred by the second liquid and is thereby uniformly mixed with the second liquid. Also, the liquid sample and the second liquid are mixed with each other in an accurate mixing ratio.

11 Claims, 5 Drawing Sheets

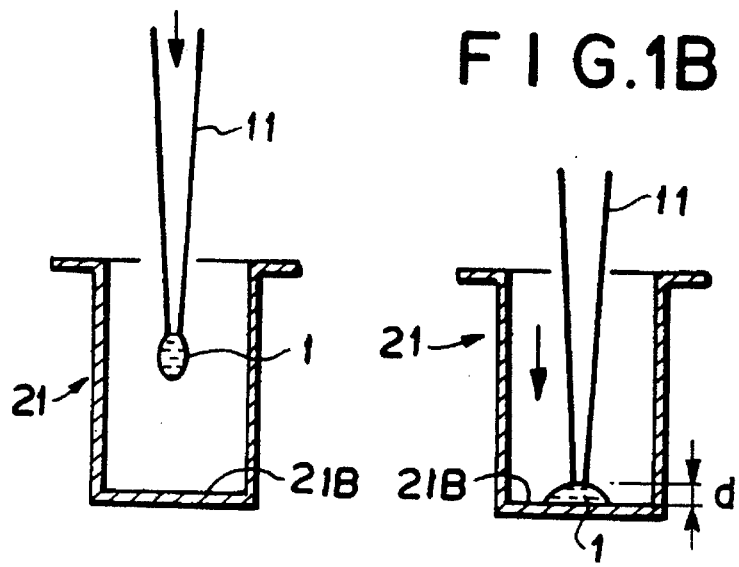
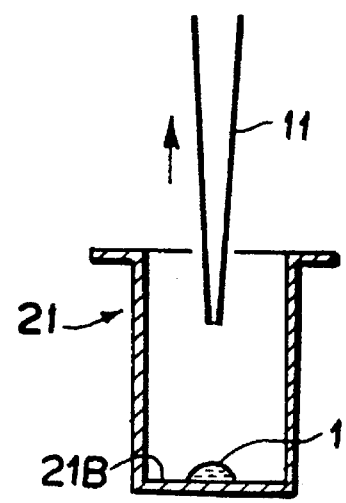
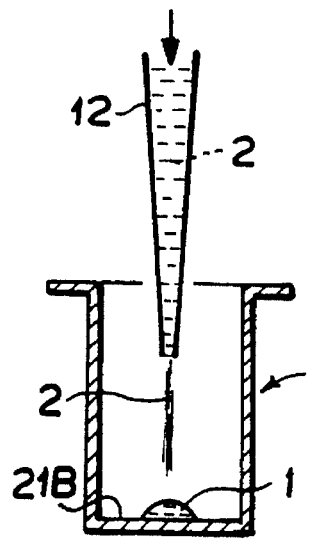
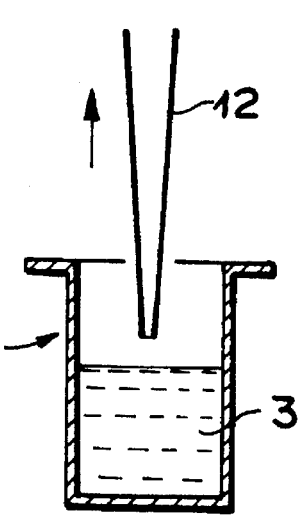

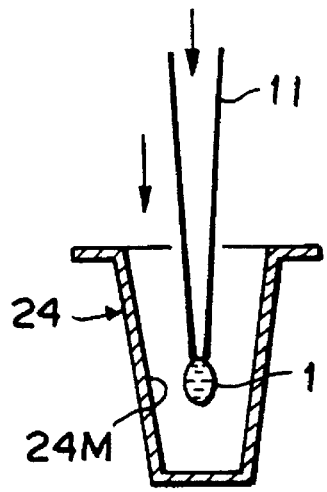
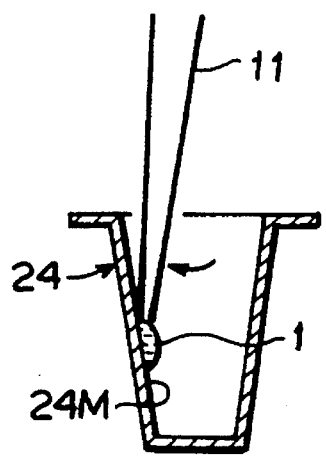
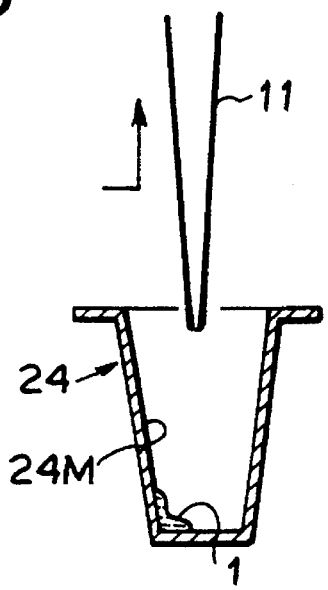
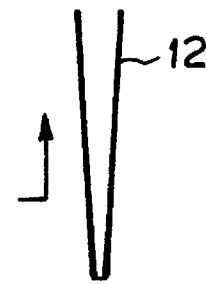
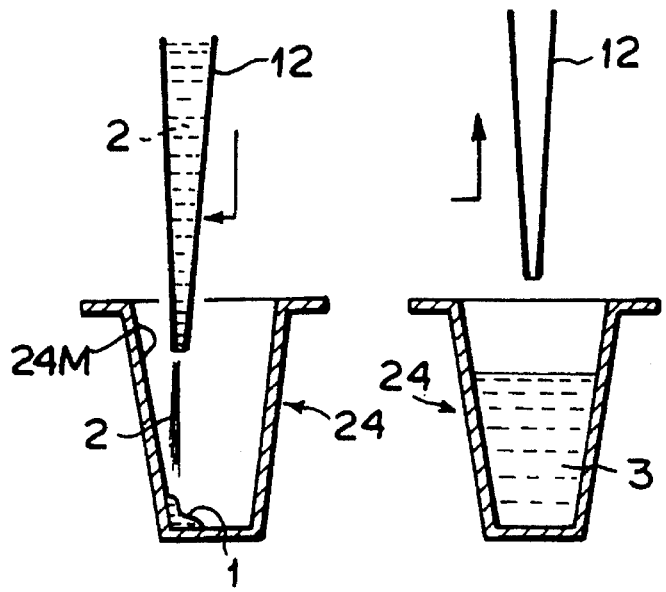

LIQUID MIXING METHOD

BACKGROUND OF THE INVENTION

1. Field of the Invention

This invention relates to a liquid mixing method, wherein a small amount of a liquid sample, such as blood, is efficiently mixed with a second liquid, and a uniform mixed liquid is thereby obtained

2. Description of the Prior Art

By way of example, with biochemical analytical apparatuses, a liquid sample, such as blood, is diluted with a predetermined diluent liquid, and a droplet of the resulting mixed liquid is applied to an analytical film having a reagent layer and is thus subjected to a reaction with the reagent layer of the analytical film. In this manner, the content or the activity of a specific chemical constituent, which is contained in the liquid sample, or the content of a physical constituent in the liquid sample is quantitatively analyzed in accordance with the results of the reaction of the chemical or physical constituent (an analyte) contained in the liquid sample and the reagent contained in the reagent layer. In such cases, a small amount (approximately 10 µl) of the liquid sample is diluted with a larger amount (approximately 200 µl) of the diluent liquid, and a predetermined amount (approximately 10 µl) of the resulting mixed liquid is applied to the analytical film.

In general, the stirring of the mixed liquid is carried out by immersing the stirring blade, which is rotated by a motor, in the mixed liquid. However, with such a technique, the stirring blade must be washed each time it has been used for stirring a liquid sample, and facilities for supplying and discharging the washing liquid must be installed. Therefore, the mechanism for the stirring of the mixed liquid cannot be kept simple, and the cost of the mechanism cannot be kept low. Alternatively, the stirring of the mixed liquid may be carried out by giving vibrations to the mixed liquid or to the vessel containing the mixed liquid. As another alternative, the stirring of the mixed liquid may be carried out by blowing a gas, which is inert with respect to the mixed liquid and is clean, to the mixed liquid. However, with these known techniques, the mechanism for the stirring of the mixed liquid cannot be kept simple, and the cost of the mechanism cannot be kept low.

As a method for diluting a liquid sample, a method for diluting a highly viscous liquid has been proposed in, for example, PCT Patent Publication WO 93/07495. The proposed method comprises the steps of introducing a diluent liquid into a vessel, inserting the orifice (i.e., the leading end) of a pipette tip, which contains a liquid sample, into the diluent liquid contained in the vessel, sucking the diluent liquid into the pipette tip, discharging the resulting mixed liquid from the pipette tip into the vessel, repeating the suction and the discharging operation, and thereby mixing the liquid sample and the diluent liquid. With the proposed method, the first stage of the dilution is carried out by utilizing the region inside of the pipette tip.

However, with the conventional liquid mixing method, such as that described above, it is not always possible to efficiently carry out uniform mixing of a liquid sample and a second liquid.

Specifically, in cases where a predetermined amount of a liquid sample is accommodated in a pipette tip and is fed into a mixing vessel, if the amount of the liquid sample to be fed into the vessel is small, a droplet of the liquid sample will be merely formed at the orifice of the pipette tip and cannot be separated and fed from the orifice of the pipette tip. Therefore, it is necessary for a particular operation to be carried out in order to transfer the droplet of the liquid sample into the vessel.

In cases where the second liquid to be mixed with the liquid sample is first fed into the vessel and thereafter the liquid sample is fed into the vessel, the droplet of the liquid sample will be brought into contact with the surface of the second liquid contained in the vessel and will thereby be transferred to the second liquid. However, the height of the surface of the second liquid fluctuates in accordance with a change in the mixing ratio of the second liquid to the liquid sample, a change in the shape of the vessel, and the like. If the height, at which the droplet of the liquid sample is brought into contact with the second liquid, is not adjusted appropriately in accordance with the fluctuation of the height of the surface of the second liquid, the amount of the droplet of the liquid sample, which is transferred to the second liquid, will fluctuate. Therefore, errors in the accuracy, with which the amount of the liquid sample to be fed is measured, become large. The errors are magnified by the mixing ratio of the second liquid to the liquid sample, and the mixing accuracy becomes low as a whole. Also, if the pipette tip for feeding the liquid sample to the second liquid is immersed into the second liquid and is then used to again suck up a new portion of the liquid sample, the problems will occur in that the remaining portion of the liquid sample to be sucked up later is contaminated with the second liquid sticking to the portion of the pipette tip, which was immersed into the second liquid.

In cases where the liquid sample is a blood corpuscle component, or the like, the liquid sample has a high viscosity and a low solubility in the second liquid. Particularly, if the liquid sample is merely fed to the second liquid, little mixing effects will be achieved, and the liquid sample will sediment and stagnate at the bottom of the vessel. Therefore, if the positive mixing operations, such as the suction and discharging operations utilizing the liquid sample pipette tip as in the conventional technique described above, are not carried out, uniform mixing of the liquid sample and the second liquid cannot be achieved. Also, even if the pipette tip is used to suck up the same liquid sample, the pipette tip must be exchanged with a new one after being used to feed the liquid sample to the second liquid. As described above, if the pipette tip is not exchanged with a new one after being used to feed the liquid sample to the second liquid, the problems with regard to the contamination of the liquid sample will occur. Therefore, the liquid mixing operations cannot be kept simple.

SUMMARY OF THE INVENTION

The primary object of the present invention is to provide a liquid mixing method, wherein a small amount of a liquid sample is efficiently stirred by a second liquid and is thereby uniformly mixed with the second liquid.

Another object of the present invention is to provide a liquid mixing method, wherein a liquid sample and a second liquid are mixed with each other in an accurate mixing ratio.

The present invention provides a liquid mixing method, wherein a small amount of a liquid sample is mixed with a second liquid, the method comprising the steps of:

i) feeding the liquid sample into a mixing vessel, and ii) thereafter discharging the second liquid from an orifice (i.e., a leading end) of a pipette tip into the vessel, the liquid sample and the second liquid being thereby stirred with each other, whereby a substantially uniform mixed liquid is prepared.

The present invention also provides a liquid mixing method, wherein a small amount of a liquid sample is mixed with a second liquid, the method comprising the steps of:

i) feeding the liquid sample into a mixing vessel, ii) thereafter discharging the second liquid from an orifice (i.e., a leading end) of a second liquid pipette tip into the vessel, a mixed liquid of the liquid sample and the second liquid being thereby formed in the vessel, and iii) carrying out, at least one time, a process for sucking the mixed liquid, which is contained in the vessel, through the orifice of the second liquid pipette tip, from which the second liquid was discharged into the vessel, into the region inside of the second liquid pipette tip, and thereafter discharging the sucked mixed liquid from the orifice of the second liquid pipette tip into the vessel, the liquid sample and the second liquid being thereby stirred with each other, whereby a substantially uniform mixed liquid is prepared.

In the liquid mixing method in accordance with the present invention, the mixed liquid may be sucked up and supported in the region inside of the second liquid pipette tip, which was used in order to feed the second liquid into the vessel, and may thereafter be fed out from the orifice of the second liquid pipette tip in a next step.

With the liquid mixing method in accordance with the present invention, a small amount of the liquid sample is fed into the mixing vessel before the second liquid is discharged into the vessel. Therefore, even if the mixing ratio of the second liquid to the liquid sample varies, the liquid sample can be fed from a predetermined height into the vessel. Therefore, the accuracy, with which the amount of the liquid sample to be fed is measured, can be kept high, and a mixed liquid containing the second liquid and the liquid sample in a desired mixing ratio can be obtained accurately. Also, after the liquid sample has been fed into the vessel, the second liquid is discharged from the orifice of the pipette tip into the vessel, and the liquid sample is thereby stirred with the second liquid. Therefore, markedly better mixing performance can be obtained than when the liquid sample is fed into the second liquid. As a result, a mixed liquid, in which the liquid sample has been mixed uniformly with the second liquid, can be obtained.

Specifically, an amount of the second liquid, which is identical with or larger than the amount of the liquid sample, is discharged quickly from the orifice of the pipette tip. In this manner, a turbulent flow of the second liquid is formed, and the mixing is carried out efficiently with the action of the turbulent flow of the second liquid.

Also, with the liquid mixing method in accordance with the present invention, the liquid sample and the second liquid may be stirred with each other by carrying out, at least one time, the process for sucking the mixed liquid, which is contained in the vessel, through the orifice of the second liquid pipette tip, from which the second liquid was discharged into the vessel, into the region inside of the second liquid pipette tip, and thereafter discharging the sucked mixed liquid from the orifice of the second liquid pipette tip into the vessel. In such cases, better mixing performance can be obtained, and a uniform mixed liquid can be obtained.

Further, with the liquid mixing method in accordance with the present invention, the mixed liquid may be sucked up and supported in the region inside of the second liquid pipette tip, which was used in order to feed the second liquid into the vessel, and may thereafter be fed out from the orifice of the second liquid pipette tip in the next step. In such cases, the working efficiency can be kept high.

When the liquid sample is to be fed into the vessel, a droplet of the liquid sample may be formed at the orifice of the liquid sample pipette tip, and the liquid sample pipette tip may then be moved until the droplet of the liquid sample formed at the orifice of the liquid sample pipette tip comes into contact with an inner bottom surface or an inner side wall surface of the vessel. In this manner, the droplet of the liquid sample may be fed to the inner bottom surface or the inner side wall surface of the vessel. In such cases, the feed of a predetermined amount of the liquid sample can be carried out easily. Alternatively, the liquid sample pipette tip may be moved to a position, at which the distance between the orifice of the liquid sample pipette tip and the inner bottom surface or the inner side wall surface of the vessel is shorter than the length of the droplet of the liquid sample. A small amount of the liquid sample may then be discharged from the liquid sample pipette tip and may thereby be fed into the vessel. In such cases, the liquid sample can be fed appropriately into the vessel. A mixing vessel utilized in accordance with the present invention may have a substantially flat plane-like bottom surface or a gentle curved surface-like bottom surface. The mixing vessel may additionally have a downwardly-tapered conical or pyramidal side wall surface.

With the liquid mixing method in accordance with the present invention, a diluent liquid for the liquid sample may be employed as the second liquid, and the liquid sample can thereby be diluted uniformly. Examples of the diluent liquids for the liquid sample include pure water; deionized water; distilled water; an aqueous physiological saline solution; an aqueous physiological saline solution containing a pH buffer; an aqueous solution containing albumin or globulin, which originates from animals (mainly man or mammals), and containing physiological saline and a pH buffer; an organic solvent, such as methanol or ethanol; and a mixture of water or one of the above-enumerated aqueous solutions and one of the above-enumerated organic solvents. These diluent liquids can also be employed as a liquid to be mixed with the liquid sample.

With the liquid mixing method in accordance with the present invention, pretreatment of the liquid sample can be carried out by using a pretreating liquid for the liquid sample as the second liquid. Examples of the pretreating liquids include an aqueous liquid and a mixture of water and an organic solvent, which contain a reagent constituent for inactivating, removing, separating, or fractionating an interfering constituent contained in the liquid sample. Table 1 shows the examples of the pretreating liquids.

TABLE 1

| Liquid sample | Object of assay | Constituent for separating, fractionating or removing interfering constituents | Pre-treating liquid |
| --- | --- | --- | --- |
| Blood | Creatinine | Endogenous ammonia | GlDH, $\alpha$-KG, NADH containing aqueous solution |
| Blood | Ammonia | Endogenous ammonia | GlDH, $\alpha$-KG, NADH containing aqueous solution |
| Blood | HDL-CHO | VLDL-CHO, LDL-CHO | Aqueous dextran sulfate-$MgCl_2$ solution |
| Blood | Constituent in plasma | Solid constituent such as erythrocyte | Lectin-containing aqueous solution |

TABLE 1-continued

| Liquid sample | Object of assay | Constituent for separating, fractionating or removing interfering constituents | Pre-treating liquid |
|---|---|---|---|

GlDH: Glutamic acid dehydrogenase
α-KG: α-Ketoglutaric acid
CHO: Cholesterol

BRIEF DESCRIPTION OF THE DRAWINGS

FIGS. 1A, 1B, 1C, 1D, and 1E are explanatory views showing how liquids are mixed with each other in a first embodiment of the liquid mixing method in accordance with the present invention, FIGS. 4A, 4B, 4C, 4D, and 4E are explanatory views showing how liquids are mixed with each other in a fourth embodiment of the liquid mixing method in accordance with the present invention.

DESCRIPTION OF THE PREFERRED EMBODIMENTS

Figure 2A:
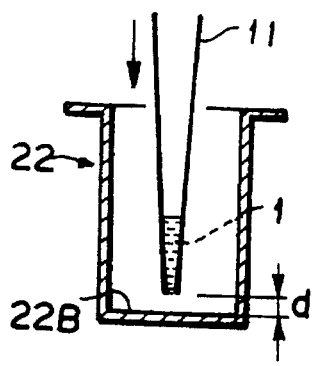
FIGS. 2A through 2I are explanatory views showing how liquids are mixed with each other in a second embodiment of the liquid mixing method in accordance with the present invention.

The present invention will hereinbelow be described in further detail with reference to the accompanying drawings.

FIGS. 1A, 1B, 1C, 1D, and 1E show how liquids are mixed with each other in a first embodiment of the liquid mixing method in accordance with the present invention. First, a mixing vessel 21 is located at a position for feeding of a liquid sample 1, and a small amount of the liquid sample 1 is fed into the vessel 21. The liquid sample 1 has been sucked up and accommodated in a liquid sample pipette tip 11, which is fitted to the orifice of a suction nozzle (not shown). As illustrated in FIG. 1A, the orifice of the liquid sample pipette tip 11 is inserted into the vessel 21. Air is then supplied into the liquid sample pipette tip 11, and the liquid sample 1 is thereby caused to flow out of the orifice of the liquid sample pipette tip 11. In this manner, a droplet of the liquid sample 1 is formed at the orifice of the liquid sample pipette tip 11. Thereafter, as illustrated in FIG. 1B, the liquid sample pipette tip 11 is moved down, and the orifice of the droplet of the liquid sample 1 is brought into contact with an inner bottom surface 21B of the vessel 21. The liquid sample pipette tip 11 is further moved down and stopped at the position, at which the distance between the orifice of the liquid sample pipette tip 11 and the inner bottom surface 21B of the vessel 21 is equal to a specified value d. Thereafter, as illustrated in FIG. 1C, the liquid sample pipette tip 11 is moved up. As a result, the droplet of the liquid sample 1 clings to the inner bottom surface 21B of the vessel 21 and is separated from the orifice of the liquid sample pipette tip 11. In this manner, the entire droplet of the liquid sample 1 is fed into the vessel 21 without remaining in the region inside of the liquid sample pipette tip 11.

The specified value d described above represents the distance, which is shorter than the vertical length of the droplet of the liquid sample 1 formed at the orifice of the liquid sample pipette tip 11. The specified value d ordinarily falls within the range of approximately ⅕ to approximately ⅘ of the vertical length of the droplet of the liquid sample 1, and should preferably fall within the range of approximately ½ to approximately ⅘ of the vertical length of the droplet of the liquid sample 1.

The vertical length of the droplet of the liquid sample 1 will vary slightly in accordance with differences in the viscosity and the surface tension of the liquid sample and differences in the hydrophobic properties and the hydrophilic properties of the surface of the outer wall in the vicinity of the orifice of the pipette tip and the surface of the orifice of the pipette tip. Specifically, in cases where the inner diameter of the orifice of the liquid sample pipette tip 11 falls within the range of 0.4 mm to 0.6 mm and the outer diameter of the orifice falls within the range of 1.0 mm to 1.2 mm, the vertical length of the droplet of the liquid sample 1 and the specified value d will take the values described below.

In cases where the liquid sample is aqueous and the amount of the droplet of the aqueous liquid sample is 10 μl, the vertical length of the droplet of the aqueous liquid sample falls within the range of approximately 3.0 mm to approximately 3.3 mm. Therefore, the specified value d ordinarily falls within the range of approximately 0.6 mm to approximately 2.7 mm, and should preferably fall within the range of approximately 1.5 mm to approximately 2.7 mm.

In cases where the liquid sample is aqueous and the amount of the droplet of the aqueous liquid sample is 4 μl, the vertical length of the droplet of the aqueous liquid sample falls within the range of approximately 1.8 mm to approximately 2.1 mm. Therefore, the specified value d ordinarily falls within the range of approximately 0.4 mm to approximately 1.7 mm, and should preferably fall within the range of approximately 0.9 mm to approximately 1.7 mm.

The liquid sample pipette tip 11 may accommodate therein an amount of the liquid sample 1 larger than the amount to be fed with a single feeding operation (i.e., may accommodate therein a large amount of the liquid sample 1 capable of being fed into a plurality of vessels), such that the liquid sample 1 can be fed successively into a plurality of vessels 21, 21, . . . Also, as a means for accurately transferring the small amount of the liquid sample 1 into the vessel 21, vibrations may be given to the liquid sample pipette tip 11 or the vessel 21.

Thereafter, the vessel 21 or a second liquid pipette tip 12, which accommodates a second liquid 2 serving as a diluent liquid therein, is moved. In this manner, as illustrated in FIG. 1D, the orifice of the second liquid pipette tip 12 is located at the position facing the vessel 21. The second liquid 2 is then discharged from the second liquid pipette tip 12 into the vessel 21. The liquid sample 1, which has been fed into the vessel 21, is stirred by the action of the second liquid 2 discharged from the second liquid pipette tip 12, and a predetermined amount of the second liquid 2 is thus fed into the vessel 21. In this manner, as illustrated in FIG. 1E, a mixed liquid 3 containing the second liquid 2 and the liquid sample 1 in a predetermined mixing ratio is obtained.

The predetermined amount of the second liquid 2 may be fed into the vessel 21 with a single continuous feeding operation or may be fed intermittently. Also, the predetermined amount of the second liquid 2, which amount corresponds to the mixing ratio of the second liquid 2 to the liquid sample 1, may be accommodated in the second liquid pipette tip 12, and all of the accommodated amount of the second liquid 2 may be discharged from the second liquid pipette tip 12 into the vessel 21. Alternatively, an amount of the second liquid 2 larger than the predetermined amount may be accommodated in the second liquid pipette tip 12, and only the predetermined amount of the second liquid 2 may be discharged from the second liquid pipette tip 12 into the vessel 21.

The height of the orifice of the second liquid pipette tip 12 should preferably be set such that the orifice may not come into contact with the surface of the mixed liquid 3 after the second liquid 2 has been discharged from the second liquid pipette tip 12 into the vessel 21. In such cases, the same second liquid pipette tip 12 can be used repeatedly in order to suck up the second liquid 2 and discharge it to a different liquid sample 1.

With the first embodiment of the liquid mixing method in accordance with the present invention, the liquid sample 1 can be fed accurately into the vessel 21. Also, the operation for stirring and mixing of the liquid sample 1 and the second liquid 2 can be carried out appropriately by the action of the second liquid 2 being discharged from the second liquid pipette tip 12 into the vessel 21. Therefore, the mixed liquid 3 having uniform concentration can be obtained.

A second embodiment of the liquid mixing method in accordance with the present invention will be described hereinbelow with reference to FIGS. 2A through 2I. In this embodiment, a mixing vessel 22, which is of the same type as the vessel 21 employed in the first embodiment, is located at a position for feeding of the liquid sample 1. As illustrated in FIG. 2A, the orifice of the liquid sample pipette tip 11, which accommodates the liquid sample 1 therein, is inserted into the vessel 22. The liquid sample pipette tip 11 is then moved down and stopped at the position, at which the distance between the orifice of the liquid sample pipette tip 11 and the inner bottom surface 22B of the vessel 22 is equal to the specified value d. The specified value d is set so as to fall within the same distance range as that in the first embodiment.

Figure 2B:
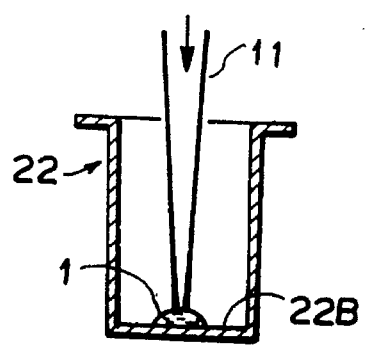
Figure 2C:
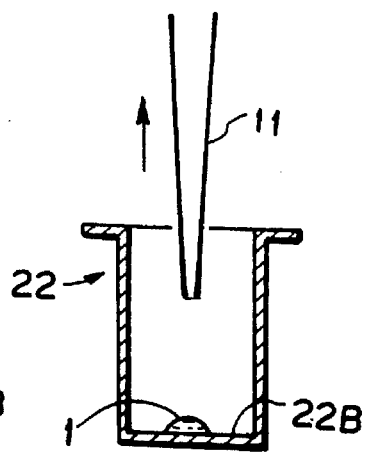

Thereafter, as illustrated in FIG. 2B, air is supplied into the liquid sample pipette tip 11, and the liquid sample 1 is thereby caused to flow out of the orifice of the liquid sample pipette tip 11. In this manner, a droplet of the liquid sample 1 is formed at the orifice of the liquid sample pipette tip 11. The droplet of the liquid sample 1 thus formed comes into contact with the inner bottom surface 22B of the vessel 22. As illustrated in FIG. 2C, the liquid sample pipette tip 11 is then moved up. As a result, the droplet of the liquid sample 1 clings to the inner bottom surface 22B of the vessel 22 and is separated from the orifice of the liquid sample pipette tip 11. In this manner, the entire droplet of the liquid sample 1 is fed into the vessel 22.

Figure 2D:
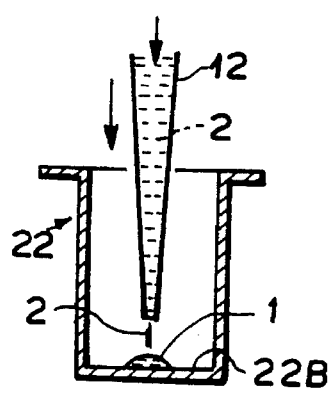
Figure 2E:
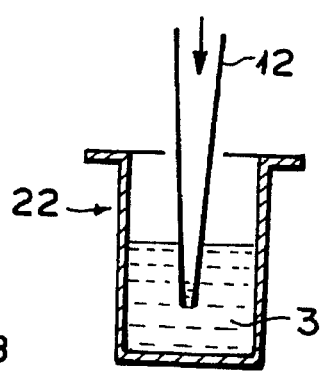
Figure 2F:
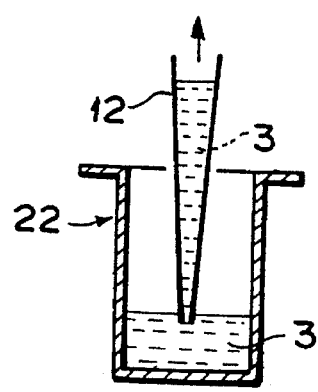
Figure 2G:
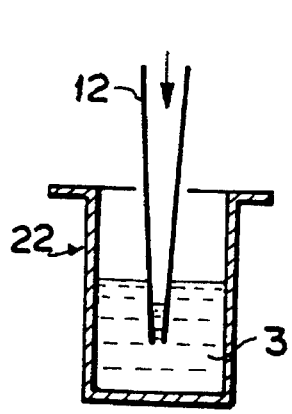

Thereafter, as illustrated in FIG. 2D, the orifice of the second liquid pipette tip 12 is located at the position facing the vessel 22. The second liquid 2 for dilution is then discharged from the second liquid pipette tip 12 into the vessel 22. At this time, the orifice of the second liquid pipette tip 12 is located at a position lower than that in the first embodiment. Specifically, as illustrated in FIG. 2E, after the second liquid 2 is discharged from the second liquid pipette tip 12 into the vessel 22, the orifice of the second liquid pipette tip 12 becomes immersed in the resulting mixed liquid 3. Thereafter, as illustrated in FIG. 2F, the mixed liquid 3 contained in the vessel 22 is sucked up by the second liquid pipette tip 12 such that the surface of the mixed liquid 3 may not become lower than the orifice of the second liquid pipette tip 12. As illustrated in FIG. 2G, the mixed liquid 3, which has thus been sucked up, is then discharged from the second liquid pipette tip 12, and the mixed liquid 3 is thereby stirred. When the mixed liquid 3 is thus discharged, the amount of the mixed liquid 3 discharged should preferably be set such that the second liquid pipette tip 12 may not become empty and the mixed liquid 3 may slightly remain in the second liquid pipette tip 12. In this manner, no air (no bubble) should be discharged from the second liquid pipette tip 12.

Figure 2H:
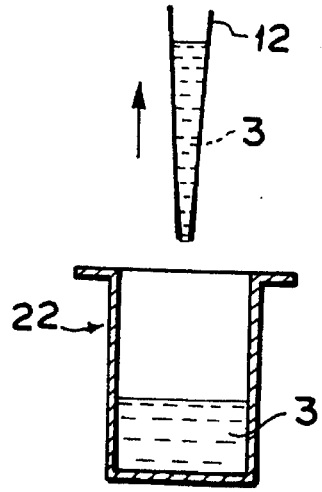
Figure 2I:
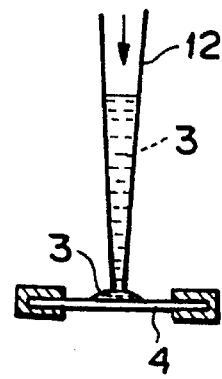

The stirring operation utilizing the second liquid pipette tip 12 in the manner described above with reference to FIGS. 2F and 2G is repeated several times, and the mixed liquid 3 containing the second liquid 2 and the liquid sample 1 in the predetermined mixing ratio is thereby obtained. Thereafter, the second liquid pipette tip 12 is utilized in order to feed the mixed liquid 3 to the next step. Specifically, as illustrated in FIG. 2H, a predetermined amount of the mixed liquid 3 is sucked up into the second liquid pipette tip 12, and thereafter the second liquid pipette tip 12 is moved upwardly from the vessel 22. As illustrated in FIG. 2I, the second liquid pipette tip 12 is then moved to a position for application of the mixed liquid 3, and a predetermined amount of the mixed liquid 3 is discharged and applied from the second liquid pipette tip 12 to a dry type of analytical element 4 for biochemical analysis.

Alternatively, as in the first embodiment, the second liquid pipette tip 12 may be located at a higher position during the discharge of the second liquid 2 into the vessel 22 and may be inserted into the resulting mixed liquid 3 during the stirring operation. When the mixed liquid 3 is stirred by repeating the suction and discharge of the mixed liquid 3 with the second liquid pipette tip 12, the amount of the mixed liquid 3 sucked up into the second liquid pipette tip 12 is set in accordance with the depth, to which the second liquid pipette tip 12 is immersed in the mixed liquid 3, or the like. Larger stirring effects can be obtained when the amount of the mixed liquid 3 sucked up into the second liquid pipette tip 12 is larger and the number of repetitions of the suction and discharge of the mixed liquid 3 with the second liquid pipette tip 12 is larger.

In this embodiment, when the liquid sample 1 is to be fed into the vessel 22, the orifice of the liquid sample pipette tip 11 is moved towards the inner bottom surface 22B of the vessel 22, and the liquid sample 1 is thereafter discharged from the orifice of the liquid sample pipette tip 11. Alternatively, the droplet of the liquid sample 1 may be formed before the orifice of the liquid sample pipette tip 11 is moved towards the inner bottom surface 22B of the vessel 22. In both cases, substantially the same liquid sample measuring accuracy can be obtained. Also, large stirring effects for the mixed liquid 3 can be obtained with the stirring operation, in which the suction and discharge of the mixed liquid 3 with the second liquid pipette tip 12 are repeated. Therefore, the second embodiment is efficient particularly in cases where the solubility of the liquid sample 1 in the second liquid 2 is low.

The stirring process in the second embodiment may be applied to the process for feeding the liquid sample 1 in the first embodiment. Also, the stirring process in the first embodiment may be applied to the process for feeding the liquid sample 1 in the second embodiment.

Figure 3A:
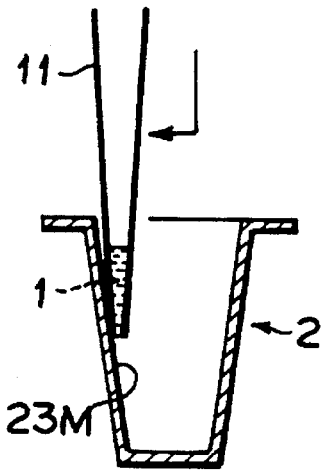
FIGS. 3A, 3B, 3C, 3D, and 3E are explanatory views showing how liquids are mixed with each other in a third embodiment of the liquid mixing method in accordance with the present invention.

A third embodiment of the liquid mixing method in accordance with the present invention will be described hereinbelow with reference to FIGS. 3A, 3B, 3C, 3D, and 3E. In this embodiment, the droplet of the liquid sample 1 is brought into contact with an inclined inner side wall surface 23M of a vessel 23. First, the vessel 23 is located at the position for feeding of the liquid sample 1. As illustrated in FIG. 3A, the orifice of the liquid sample pipette tip 11, which accommodates the liquid sample 1 therein, is then inserted into the vessel 23 and moved horizontally. In this manner, the orifice of the liquid sample pipette tip 11 is brought into contact with the inner side wall surface 23M of the vessel 23 or is located at the position close to the inner side wall surface 23M.

Figure 3B:
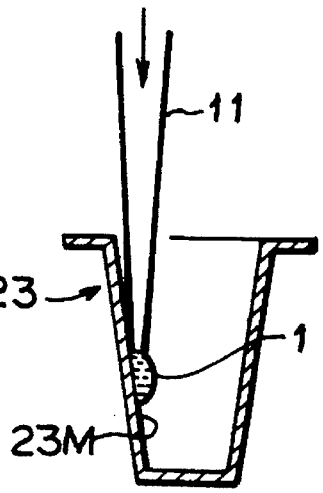
Figure 3C:
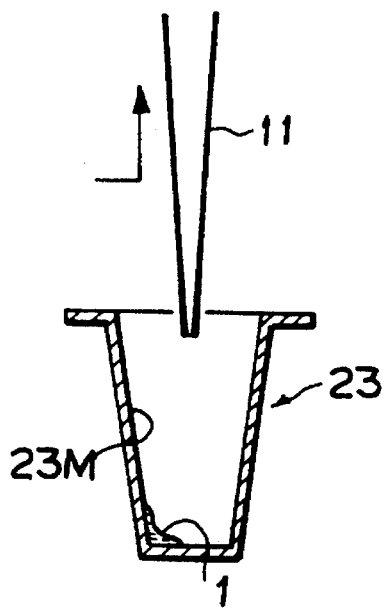

Thereafter, as illustrated in FIG. 3B, air is supplied into the liquid sample pipette tip 11, and the liquid sample 1 is thereby caused to flow out of the orifice of the liquid sample pipette tip 11. The droplet of the liquid sample 1, which has thus been discharged from the orifice of the liquid sample pipette tip 11, comes into contact with the inner side wall surface 23M of the vessel 23. Thereafter, as illustrated in FIG. 3C, the liquid sample pipette tip 11 is moved horizontally towards the center point of the vessel 23 and is then moved up. As a result, the droplet of the liquid sample 1, which clings to the inner side wall surface 23M of the vessel 23, separates from the orifice of the liquid sample pipette tip 11, flows down by gravity, and is thereby fed into the vessel 23.

Figure 3D:
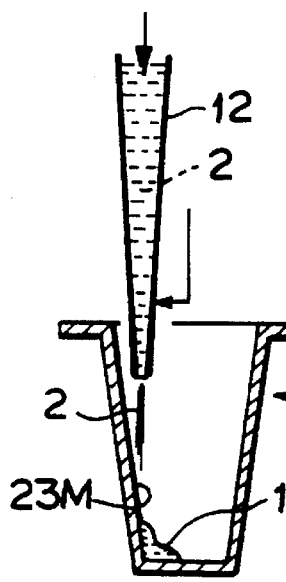
Figure 3E:
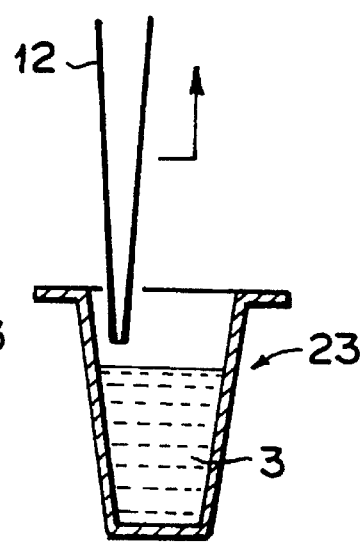

Thereafter, as illustrated in FIG. 3D, the orifice of the second liquid pipette tip 12 is located at the position facing the vessel 23, and the second liquid 2 for dilution is discharged from the second liquid pipette tip 12. In this manner, the liquid sample 1, which has been fed into the vessel 23, is stirred by the action of the second liquid 2 discharged from the second liquid pipette tip 12. At this time, the second liquid pipette tip 12 has been moved from the center point of the vessel 23 towards the inner side wall surface 23M such that the second liquid 2 can be discharged from the orifice of the second liquid pipette tip 12 towards the liquid sample 1 contained in the vessel 23. As illustrated in FIG. 3E, the mixed liquid 3 is obtained by the effects of stirring with the second liquid 2 being discharged from the orifice of the second liquid pipette tip 12. Thereafter, the second liquid pipette tip 12 is moved to the exterior of the vessel 23.

In the third embodiment, as in the first embodiment, the stirring with the second liquid pipette tip 12 is carried out by the single operation for discharging the second liquid 2 from the second liquid pipette tip 12 into the vessel 23. Alternatively, as in the second embodiment, the stirring operation may be carried out by repeating the suction and discharge of the mixed liquid 3.

Also, the orifice of the second liquid pipette tip 12 may be brought into contact with the inner side wall surface 23M of the vessel 23, and the second liquid 2 may be discharged from the orifice of the second liquid pipette tip 12. Alternatively, the second liquid pipette tip 12 may be inclined, and the second liquid 2 may be discharged obliquely from the orifice of the second liquid pipette tip 12 towards the liquid sample 1 contained in the vessel 23. Further, the liquid sample pipette tip 11 for feeding the liquid sample 1 may be inclined and brought into contact with the inner side wall surface 23M of the vessel 23 or located close to the inner side wall surface 23M.

As in the second embodiment, after the liquid sample 1 has been mixed and diluted with the second liquid 2, the second liquid pipette tip 12 may be utilized in order to suck up a predetermined amount of the resulting mixed liquid 3. A predetermined amount of the mixed liquid 3 may then be discharged and applied from the second liquid pipette tip 12 to the dry type of analytical element 4 for biochemical analysis.

With the third embodiment, the feed of the liquid sample 1 to the vessel 23 is carried out by bringing the orifice of the liquid sample pipette tip 11 into contact with the inner side wall surface 23M of the vessel 23. In cases where the liquid sample pipette tip 11 is constituted of an elastic member, such as a plastic member, even if the orifice of the liquid sample pipette tip 11 is strongly brought into contact with the inner side wall surface 23M, the problems with regard to break of the liquid sample pipette tip 11, and the like, will not occur. Therefore, in such cases, control of the movement of the liquid sample pipette tip 11 becomes easy. Also, the vessel 23 may be supported loosely such that it can move and reduce the shock between the liquid sample pipette tip 11 and the inner side wall surface 23M when the liquid sample pipette tip 11 is brought into contact with the inner side wall surface 23M. In this manner, control of the movement of the liquid sample pipette tip 11 can be kept easy.

A fourth embodiment of the liquid mixing method in accordance with the present invention will be described hereinbelow with reference to FIGS. 4A, 4B, 4C, 4D, and 4E. In this embodiment, as in the third embodiment, a vessel 24 having an inclined inner side wall surface 24M is employed. The droplet of the liquid sample 1 is brought into contact with the inner side wall surface 24M of the vessel 24. First, the vessel 24 is located at the position for feeding of the liquid sample 1. As illustrated in FIG. 4A, the orifice of the liquid sample pipette tip 11, which accommodates the liquid sample 1 therein, is inserted into the vessel 24, and a droplet of a predetermined amount of the liquid sample 1 is formed at the orifice of the liquid sample pipette tip 11.

Thereafter, as illustrated in FIG. 4B, the liquid sample pipette tip 11 is inclined such that its orifice may move horizontally towards the inner side wall surface 24M of the vessel 24. In this manner, the droplet of the liquid sample 1 formed at the orifice of the liquid sample pipette tip 11 is brought into contact with the inner side wall surface 24M of the vessel 24. The orifice of the liquid sample pipette tip 11 is thus brought into contact with the inner side wall surface 24M or is located close to the inner side wall surface 24M. Thereafter, as illustrated in FIG. 4C, the liquid sample pipette tip 11 is moved horizontally towards the center point of the vessel 24 and is then moved up. As a result, the droplet of the liquid sample 1, which clings to the inner side wall surface 24M of the vessel 24, separates from the orifice of the liquid sample pipette tip 11 and is thereby fed into the vessel 24.

Thereafter, as illustrated in FIG. 4D, the orifice of the second liquid pipette tip 12 is located in an inclined orientation at the position facing the vessel 24, and the second liquid 2 for dilution is discharged from the second liquid pipette tip 12 towards the liquid sample 1, which has been fed into the vessel 24. In this manner, the liquid sample 1, which has been fed into the vessel 24, is stirred by the action of the second liquid 2 discharged from the second liquid pipette tip 12. In this manner, as illustrated in FIG. 4E, the mixed liquid 3 is obtained. Thereafter, the second liquid pipette tip 12 is moved to the exterior of the vessel 24.

In the fourth embodiment, as in the first embodiment, the stirring with the second liquid pipette tip 12 is carried out by the single operation for discharging the second liquid 2 from the second liquid pipette tip 12 into the vessel 24. Alternatively, as in the second embodiment, the stirring operation may be carried out by repeating the suction and discharge of the mixed liquid 3.

With the embodiment, wherein the liquid sample pipette tip 11 is inclined in order to bring the droplet of the liquid sample 1 into contact with the inner side wall surface 24M of the vessel 24, it is possible to employ the cylindrical vessel 22 used in the first embodiment, and the droplet of the liquid sample 1 can be brought into contact with the inner side wall surface of the cylindrical vessel 22. Also, in cases where the inner bottom surface of the vessel having the inclined inner side wall surface 24M is flat, the liquid sample 1 can be fed into the vessel 24 by being brought into contact with the inner bottom surface of the vessel 24 as in the first and second embodiments.

As in the embodiments described above, in order for good stirring and mixing performance to be obtained with the discharge of the second liquid 2 to the liquid sample 1, the vessels 21, 22, 23, and 24 should preferably have a shape such that the depth is large with respect to the opening area and a turbulent flow of the discharged second liquid 2 can readily occur.

Figure 5:
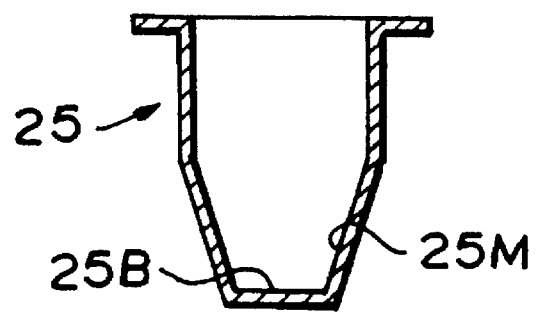
FIG. 5 is a cross-sectional view showing an example of a mixing vessel.

FIG. 5 shows an example of a mixing vessel, which may be employed in the liquid mixing method in accordance with the present invention. With reference to FIG. 5, a vessel 25 has a shape such that only the lower half of the inner side wall surface is inclined. The vessel 25 has an inner bottom surface 25B and an inclined side wall surface 25M. The vessel 25 can be employed in the embodiments described above and has good stirring and mixing performance with the discharge of the second liquid 2 to the liquid sample 1.

The inner bottom surface or the inner side wall surface of each of the vessels 21, 22, 23, 23, and 25, which surface receives the droplet of the liquid sample 1, should preferably be rendered rough such that the surface can snugly fit to the droplet of the liquid sample 1 and can readily receive it.

Figure 6:
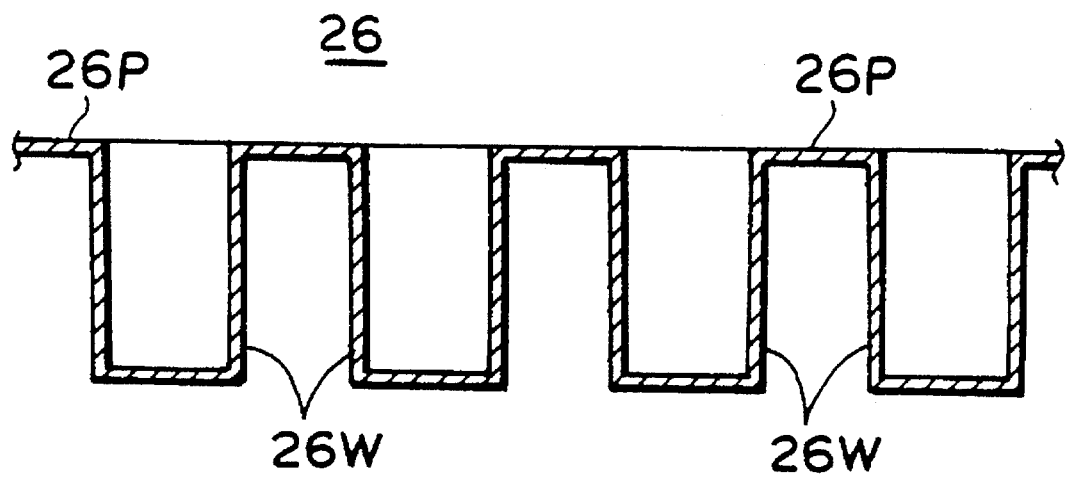
FIG. 6 is a cross-sectional view showing a different example of a mixing vessel.

FIG. 6 shows a different example of a mixing vessel, which may be employed in the liquid mixing method in accordance with the present invention. With reference to FIG. 6, a vessel 26 comprises a plurality of recesses (wells) 26W, 26W, ..., which are formed continuously and have the flat bottom shape as in the vessel 21 employed in the first embodiment. The plurality of the recesses (wells) 26W, 26W, ..., which constitute the vessels, are formed in a plate 26P with a molding process. The vessel 26 is thus formed as a well plate as a whole. The vessel 26 is built in an inspection device, or the like, such that it can rotate. The vessel 26 can thus be appropriately utilized in order to continuously mix various kinds of liquid samples 1 with a second liquid.

As for the embodiments described above, the mixing performance was measured. The results obtained will be described hereinbelow.

In Examples 1, 2, and 3 of the liquid mixing method in accordance with the present invention, the vessel 26 shown in FIG. 6 was used. Each of the recesses 26W, 26W, ... had an upper end inner diameter of 7.0 mm, a bottom inner diameter of 6.4 mm, a depth of 11.25 mm, and a volume of 0.396ml. The vessel 26 was constituted of a polystyrene. First, a small amount (10 µl) of a liquid sample containing C-reactive protein (CRP) was fed into the recess 26W. Thereafter, a predetermined amount (200 µl) of an aqueous 20mM n-morpholinoethanesulfonic acid (MES) buffer solution having a pH value of 6.0, which served as a second liquid for dilution, was discharged into the recess 26W. The mixing conditions were as shown below.

| Example 1 | |
|---|---|
| Pouring of the second liquid: | 200 µl × 1 time after the liquid sample had been fed. |
| Stirring operation: | None |
| Example 2 | |
| Pouring of the second liquid: | 200 µl × 1 time after the liquid sample had been fed. |
| Stirring operation: | 200 µl × 5 times |
| Example 3 | |
| Pouring of the second liquid: | 100 µl × 2 times after the liquid sample had been fed. |
| Stirring operation: | 100 µl × 5 times |

Specifically, in Example 1, 200 µl of the second liquid was discharged at one time into the recess 26W as in the first embodiment described above. In Example 2, after 200 µl of the second liquid was discharged at one time into the recess 26W, the stirring operation was carried out with the suction and discharge of the mixed liquid with the second liquid pipette tip as in the second embodiment. During the stirring operation, 200 µl of the mixed liquid was sucked up and was then discharged. The suction and discharge were repeated five times. In Example 3, after two 100 µl portions of the second liquid were discharged with two independent operations into the recess 26W, the stirring operation was carried out with the suction and discharge of the mixed liquid with the second liquid pipette tip. During the stirring operation, 100 µl of the mixed liquid was sucked up and was then discharged. The suction and discharge were repeated five times.

In Comparative Examples 1 and 2, the vessel 26 was used, and 200 µl of the second liquid was poured into the recess 26W. Thereafter, a small amount (10 µl) of the liquid sample was fed into the recess 26W. The mixing conditions were as shown below.

| Comparative Example 1 | |
|---|---|
| Pouring of the second liquid: | 200 µl × 1 time before the liquid sample was fed. |
| Stirring operation: | None |
| Comparative Example 2 | |
| Pouring of the second liquid: | 200 µl × 1 time before the liquid sample was fed. |
| Stirring operation: | 10 µl × 5 times |

Specifically, in Comparative Example 1, the liquid sample was merely dropped into the second liquid. In Comparative Example 2, after the liquid sample was dropped into the second liquid, the stirring operation was carried out with the suction and discharge of the mixed liquid with the second liquid pipette tip. During the stirring operation, 10 µl of the mixed liquid was sucked up and was then discharged. The suction and discharge were repeated five times.

In the manner described above, the mixed liquids were formed in 10 recesses 26W, 26W, ... of the vessel 26. Thereafter, 10 µl portions of the respective mixed liquids were successively sucked up and applied to 10 dry type analytical elements, and the concentrations of the liquid sample in the respective mixed liquids were measured (in units of mg/dl). At this time, the value of the concentration measured for the mixed liquid, which was sucked up from the upper region of each recess 26W, and the value of the concentration measured for the mixed liquid, which was sucked up from the lower region of the recess 26W, were compared with each other. Also, the amount of dispersion in the measured concentrations was investigated. In this manner, a judgment was made as to the uniformity of the stirring. Specifically, if the value of the concentration measured for the mixed liquid in the upper region of each recess 26W and the value of the concentration measured for the mixed liquid in the lower region of the recess 26W are equal to each other, it can be judged that the liquid has been mixed uniformly in the recess 26W. If the amount of dispersion in the measured concentrations is small, it can be judged that good mixing effects were obtained uniformly among the recesses 26W, 26W, ... of the vessel 26.

The results of the measurements shown in Table 2 were obtained. The mean value $\bar{X}$ represents the simple mean value (mg/dl) of 10 measured concentrations. The CV (Coefficient of Variation) value (%) represents the amount of dispersion. A larger CV value represents a larger amount of dispersion.

TABLE 2

|  |  | Mixed liquid from upper region | Mixed liquid from lower region |
| --- | --- | --- | --- |
| Example 1 | $\bar{X}$ | 3.63 | 3.77 |
|  | CV | 5.52 | 4.52 |
| Example 2 | $\bar{X}$ | 3.48 | 3.50 |
|  | CV | 5.38 | 6.02 |
| Example 3 | $\bar{X}$ | 3.52 | 4.11 |
|  | CV | 4.40 | 5.43 |
| Comp. Ex. 1 | $\bar{X}$ | 1.05 | 5.79 |
|  | CV | 145.3 | 24.16 |
| Comp. Ex. 2 | $\bar{X}$ | 5.57 | 6.51 |
|  | CV | 36.29 | 17.58 |

From the results shown in Table 2, it can be found that, in Examples 1, 2, and 3, the measured value ($\bar{X}$) for the mixed liquid, which was sucked up from the upper region of each recess 26W, and the measured value ($\bar{X}$) for the mixed liquid, which was sucked up from the lower region of the recess 26W, are approximately identical with each other, and the CV value is small regardless of the position, from which the mixed liquid was sucked up. Therefore, it can be found that, in Examples 1, 2, and 3, the liquid sample and the second liquid were uniformly mixed with each other. Particularly, in Example 1, good diluting and stirring effects were obtained. Therefore, the effects of the stirring operation in Example 2 could not be confirmed clearly. Whether the stirring operation is or is not necessary may be determined in accordance with the shape of the vessel, the volume of the vessel, and the physical properties (the specific gravity, the viscosity, and the like) of the liquid sample.

On the other hand, in Comparative Example 1, the measured value ($\bar{X}$) for the mixed liquid, which was sucked up from the upper region of each recess 26W, is markedly smaller than the measured value ($\bar{X}$) for the mixed liquid, which was sucked up from the lower region of the recess 26W. Also, the CV value is very large, and a large amount of dispersion is found in the measured concentrations. Therefore, it can be found that, in Comparative Example 1, the liquid sample was not diffused in the second liquid. This is because the liquid sample, which is added merely to the second liquid, sediments to the region in the vicinity of the bottom of each recess 26W and is thereafter dissolved very slowly. In Comparative Example 2, wherein the stirring operation is carried out, the difference between the measured value ($\bar{X}$) for the mixed liquid, which was sucked up from the upper region of each recess 26W, and the measured value ($\bar{X}$) for the mixed liquid, which was sucked up from the lower region of the recess 26W, is smaller than in Comparative Example 1. However, with Comparative Example 2, the CV value is large, and a large amount of dispersion is found in the measured concentrations. If the amount of the mixed liquid sucked up and discharged during the stirring operation is increased, the stirring effects will become larger. However, more stirring operations are required in order to achieve as uniform stirring as in Examples of the liquid mixing method in accordance with the present invention.

In the liquid mixing method in accordance with the present invention, the uniformly tapered pipette tip shown in FIGS. 1 through 6 may be employed. It is also possible to employ pipette tips having various shapes, such as the pipette tips in which the diameter of the portion having a length falling within the range of approximately 2 mm to approximately 10 mm and in the vicinity of the orifice of the pipette tip is reduced to an extent ranging from approximately ½ to approximately ⅕ of the diameter of the upper portion. Such pipette tips are disclosed in, for example, U.S. Pat. No. 3,855,867 (Canadian Patent No. 999,562) and U.S. Pat. No. 4,347,875 (Canadian Patent No. 1,142,407).

What is claimed is:

1. A liquid mixing method, wherein a small amount of a liquid sample is mixed with another liquid, the method comprising the steps of:

forming a droplet of a first liquid sample at an orifice of a first pipette tip;

after forming the droplet, moving the first pipette tip to bring the first liquid sample droplet into contact with an inner surface of a mixing vessel, whereby the first liquid sample is discharged into the mixing vessel; and after discharging the first liquid sample into the mixing vessel, discharging a second liquid from an orifice of a second pipette tip to stir the first and second liquids with each other, whereby a substantially uniform mixed liquid is prepared.

2. A liquid mixing method, wherein a small amount of a liquid sample is mixed with another liquid, the method comprising the steps of:

moving a first pipette tip in a mixing vessel to a position at which the vertical distance between an orifice of the first pipette tip and an inner surface of the mixing vessel is shorter than the vertical length of a droplet of a predetermined amount of a first liquid sample;

after moving the first pipette tip, discharging the predetermined amount of the liquid sample from the pipette tip orifice into the mixing vessel; and after discharging the first liquid sample into the mixing vessel, discharging a second liquid from an orifice of a second pipette tip to stir the first and second liquids with each other, whereby a substantially uniform mixed liquid is prepared.

3. A liquid mixing method, wherein a small amount of a liquid sample is mixed with another liquid, the method comprising the steps of:

moving a first pipette tip to a position at which the distance between an orifice of the first pipette tip and an inner bottom surface of a mixing vessel falls within the range of approximately ⅕ to approximately ⅘ of the vertical length of the droplet of the liquid sample to be formed at the orifice of the first pipette tip;

after moving the first pipette tip, discharging the liquid sample from the orifice of the first pipette tip; and after discharging the first liquid sample into the mixing vessel, discharging a second liquid from an orifice of a second pipette tip to stir the first and second liquids with each other, whereby a substantially uniform mixed liquid is prepared.

4. A method as defined in claim 1, 2, or 3, further comprising the steps of:

drawing the mixed liquid from the mixing vessel into the second pipette through the orifice thereof and subsequently discharging the mixed liquid from the second pipette into the mixing vessel to further stir the first and second liquids.

5. A method as defined in claim 1, 2, or, 3, further comprising the steps of:

drawing the mixed liquid from the mixing vessel into the second pipette through the orifice thereof; and subsequently discharging the mixed liquid from the second pipette onto an analytical element.

6. A method as defined in claim 1, 2, or 3, wherein the amount of the second liquid is not smaller than the amount of the first liquid.

7. A method as defined in claim 1, 2, or 3, wherein the second liquid is a diluent liquid.

8. A method as defined in claim 1, 2, or 3, wherein the second liquid is a pretreating liquid.

9. A method as defined in claim 1, 2, or 3 wherein the mixing vessel has substantially flat plane-like bottom surface or a gentle curved surface-like inner bottom surface.

10. A method as defined in claim 9 wherein the mixing vessel has downwardly tapered conical or pyramidal side wall surface.

11. A method as defined in claim 1, 2, or 3 wherein an amount of the first liquid capable of being fed into a plurality of mixing vessels is supported in the first pipette tip, and a predetermined amount of the first liquid is discharged from the orifice of the first pipette tip into each of the plurality of vessels, the first liquid being thereby fed into each of the plurality of vessels.

* * * * *